United States Patent
Cook et al.

(10) Patent No.: US 10,675,241 B2
(45) Date of Patent: Jun. 9, 2020

(54) COMPOSITIONS CONTAINING PREEN OIL AND METHODS OF USE THEREOF

(71) Applicant: WISCONSIN ALUMNI RESEARCH FOUNDATION, Madison, WI (US)

(72) Inventors: Mark E. Cook, Madison, WI (US); Jordan Sand, Madison, WI (US); Jake M. Olson, Madison, WI (US); Terence P. Barry, Middleton, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 188 days.

(21) Appl. No.: 15/906,272

(22) Filed: Feb. 27, 2018

(65) Prior Publication Data
US 2018/0185278 A1   Jul. 5, 2018

Related U.S. Application Data

(62) Division of application No. 14/931,289, filed on Nov. 3, 2015, now Pat. No. 9,943,480.

(51) Int. Cl.
| | | |
|---|---|---|
| *A61K 36/00* | (2006.01) | |
| *A61K 9/00* | (2006.01) | |
| *A23K 10/20* | (2016.01) | |
| *A23K 20/158* | (2016.01) | |
| *A23K 50/80* | (2016.01) | |
| *A61K 35/57* | (2015.01) | |
| *A61K 45/06* | (2006.01) | |
| *A61K 31/232* | (2006.01) | |

(52) U.S. Cl.
CPC ............ *A61K 9/0056* (2013.01); *A23K 10/20* (2016.05); *A23K 20/158* (2016.05); *A23K 50/80* (2016.05); *A61K 31/232* (2013.01); *A61K 35/57* (2013.01); *A61K 45/06* (2013.01); *Y02A 40/818* (2018.01)

(58) Field of Classification Search
CPC .................................................... A61K 36/00
See application file for complete search history.

(56) References Cited

U.S. PATENT DOCUMENTS

| 4,096,262 | A | 6/1978 | Andrews et al. |
| 7,063,855 | B2 | 6/2006 | Hjaltason et al. |
| 2005/0143465 | A1 | 6/2005 | Pageat |
| 2008/0233060 | A1 | 9/2008 | Grune |
| 2010/0159113 | A1 | 6/2010 | Hayek et al. |
| 2017/0119016 | A1 | 5/2017 | Cook et al. |

FOREIGN PATENT DOCUMENTS

| CN | 104431538 A | * | 3/2015 |
| CN | 104543532 A1 | | 4/2015 |
| DE | 3341569 A1 | | 5/1985 |
| WO | 2017078997 A1 | | 5/2017 |

OTHER PUBLICATIONS

Lillard et al, Isolation and characterization of the lipids from the chicken preen gland. Journal of Food Science (1976), 41(1), 195-6 (Year: 1976).*
Ataie-Kachoie et al.; "Gene of the Month; Interleukin 6 (IL-6)"; J. Clin. Pathol; 67; pp. 932-934; (2014).
Birnbaum et al.; "Societal Cost of Rheumatoid Arthritis Patients in the US"; Current Medical Research & Opinion; 26 (1); pp. 77-90; (2010).
Butler et al.; "Anti-IL-12 and Anti-TNF Antibodies Synergistically Suppress the Progression of Murine Collagen-Induced Arthritis"; Eur. J. Immunol.; 29; pp. 2205-2212; (1999).
Caballero et al.; "Impact of Different Dietary Lipid Sources on Growth, Lipid Digestibility, Tissue Fatty Acid Compositors and Histology of Rainbow Troup, Oncorhynchus Mykiss"; Aquaculture; 214; pp. 253-271 (2002).
De Paepe et al.; "Scanning for Therapeutic Targets Within the Cytokine Network of Idiopathic Inflammatory Myopathies"; Int. J. Mol. Sci.; 16; pp. 18683-18713; (2015).
Devitt, Sara; Presence of Anti-Cancer Fatty Acid in Segregated Tissue From Animal Processing (STFAP); Biology; 152; Section 608; 11 pages; (2013).
Federici et al.; "The Central Role of Anti-IL-1 Blockage in the Treatment of Monogenic and Multi-factorial Autoinflammatory Diseases"; Frontiers in Immunology; 4, article 351, pp. 1-12; published Oct. 31, 2013.
Fukuzawa et al.; "Possible Involvement of Long Chain Fatty Acids in the Spores of Ganoderma Lucidum (Reishi Houshi) to Its Anti-Tumor Activity"; Biol. Pharm. Bull.; 31(10); pp. 1933-1937; (2008).
Gao et al.; "Isolation and Identification of C-19 Fatty Acids with Anti-Tumor Activity From the Spores of Ganoderma Lucidum (reishi muchroom)"; Fitoterapia; 83; pp. 490-499; (2012).
Hansen et al.; "Erythro-Diols of Wax from the Uropygial Gland of the Turkey"; Journal of Lipid Research; (10); pp. 267-270; (1969).
Hirao et al.; "The Role of Uropygial Gland on Sexual Behavior in Domestic Chicken Gallus gallus domesticus"; Behavioural Processes; 80; pp. 115-120; (2009).
International Search Report and Written Opinion; International Application No. PCT/US2016/058769; International Filing Date Oct. 26, 2016; dated Apr. 4, 2017; 16 pages.
Kang et al.; Therapeutic Uses of Anti-interleukin-6 Receptor Antibody; International Immunology; 27(1); pp. 21-29; Advance Access publication Aug. 20, 2014.

(Continued)

*Primary Examiner* — Qiuwen Mi
(74) *Attorney, Agent, or Firm* — Cantor Colburn LLP

(57) ABSTRACT

Described herein are methods of use of purified preen oil, food and feed compositions containing purified preen oil, food and feed additives containing purified preen oil, and pharmaceutical compositions containing purified preen oil. Methods include treatment of chronic joint inflammation in humans and animals by orally administering purified preen oil. Also included are methods of feeding a growing fish by feeding the feeding the growing fish purified preen oil in amounts effective to improve survival and/or stimulate growth in the growing fish. Further included are methods of feeding live prey organisms purified preen oil, and feeding the live prey organisms to growing fish.

24 Claims, 4 Drawing Sheets

(56) References Cited

OTHER PUBLICATIONS

Kim et al.; "The Roll of IL-12 in Inflammatory Activity of Patients with Rheumatoid Arthritis (RA)"; Clin Exp Immunol; 119; pp. 175-181; (2000).

Lakshmi et al.; "Antiperoxidative, Anti-Inflammatory, and Antimutagenic Activities of Ethanol Extract of the Mycelium of Ganoderma Lucidum Occurring in South India"; Teratogenesis,Carcinogenesis,and Mutagenesis Supplement 1; pp. 85-97; (2003).

Lillard et al.; "Isolation and Characterization of the Lipids From the Chicken Preen Gland"; Journal of Food Science; 41(1); pp. 195-196; (1976).

Matthys et al.; "Anti-IL-42 Antibody Prevents the Development and Progression of Coliagen-Induced Arthritis in IFN-γ Receptor-Deficient Mice"; Eur. J. Immunol; 28; pp. 2143-2151; (1998).

Midtlyng, P.J.; "Vaccinated Fish Welfare: Protection Versus Side-Effects" in Fish Vaccinology; Gudding R, Lillehaug A, Midtlyng PJ, Brown F (eds); Dev Biol Stand, Basel, Karger, vol. 90; pp. 371-379; (1997).

Miles et al.; "The Benefits of Fish Meal in Aquaculture Diets"; Fisheries and Aquatic Sciences Department, UF/IFAS Extension; original publication Nov. 2005; http://edis.ifas.ufl.edu.

Molto et al.; "Ati-IL-1 Molecules: New Comers and New Indications"; Joint Bone Spine; 77; pp. 102-107; (2010).

Moyer et al.; Experimental Test of the Importance of Preen Oil in Rock Doves (Columba Liva); The Auk; 120(2); pp. 490-496; (2003).

Petrovic-Rackov et al.; "Clinical Significance of IL-18, IL-15, IL-12 and TNF-a Measurement in Rheumatoid Arthritis"; Clin Rheumatol; 25; pp. 448-452; (2006).

Romarheim et al.; "Bacteria Grown on Natural Gas Prevent Soybean Meal-Induced Enteritis in Atlantic Salmon"; Journal of Nutrition; 141; pp. 124-130 (2011).

Sandilands et al.; "Preen Gland Function in Layer Fowls: Factors Affecting Preen Oil Fatty Acid Composition"; British Poultry Science; 45(1); pp. 109-115; (2004).

Shobha et al.; "Volatile Compounds of Therapeutic Importance Produced by Leuconostoc paramesenteroides, a Native Laboratory Isolate"; Turk J. Biol.; 31, pp. 35-40; 2007.

Spooren et al.; "Interleukin-6, a mental cytokine"; Brain Research Reviews; 67; pp. 157-183; (2011).

Uran et al.; "Soybean Meal Induces Intestinal Inflammation in Common Carp (*Cyprinus carpio* L.)"; Fish & Shellfish Immunology; 25; pp. 751-760; (2008).

Yoo et al.; "Characterization and Cytotoxic Activities of Nonadecanoic Acid Produced by *Streptomyces scabiei* Subsp. Chosunensis M0137 (KCTC 9927)"; Journal of Microbiology; 40(4); pp. 331-334; (2002).

* cited by examiner

COMPOSITIONS CONTAINING PREEN OIL AND METHODS OF USE THEREOF

CROSS-REFERENCE TO RELATED APPLICATIONS

This application is a divisional of U.S. application Ser. No. 14/931,289 filed on Nov. 3, 2015, which is incorporated herein by reference in its entirety.

STATEMENT REGARDING FEDERALLY SPONSORED RESEARCH & DEVELOPMENT

This invention was made with government support under 18-CRHF-0-6055 awarded by the USDA/NIFA. The government has certain rights in the invention.

FIELD OF THE DISCLOSURE

The present disclosure is related to compositions and methods for the oral administration of naturally occurring oils, particularly food and feed compositions.

BACKGROUND

The exudate from the preen (or uropygial) gland found at the base of the tail of most birds, is applied to the plumage during preening. Preen gland exudate has a lipid fraction and a non-lipid fraction containing proteins, inorganic salts and cell fragments. The lipid fraction (herein referred to as preen oil) is made up of monoester, diester and triester waxes (long-chain carbon molecules which contain one, two or three ester bonds). Preen oil isolated from turkey preen glands has been shown, for example, to include the fatty acids C10:0, C12:0, C14:0, C16:0, C17:0, C18:0, C19:0 and C20:0. In vitro assays have suggested that C19:0 (19:0 or nonadecanoic acid) has possible anti-inflammatory, anti-tumor, and proliferous cell inhibitory effects.

There is increasing interest in natural substances that have health benefits in medicine and animal agriculture. Preen glands are included in segregated tissue from animal processing (STFAP). Currently, STFAP is discarded or rendered with other wastes during meat harvest and processing, and can be separated from a larger stream of waste and by-products. The oil from the animal tissue can be easily removed through mechanical means (dissection) and extracted using solvents. It is thus desirable to isolate preen oil from preen glands that would otherwise be part of the waste stream of animal processing and to identify uses for the purified preen oil.

What is needed are methods of use of natural substances such as preen oil to provide health benefits in humans and animals.

BRIEF SUMMARY

In one aspect, a method of treating an individual in need of treatment for chronic inflammation comprises orally administering to the individual a composition comprising a therapeutically effective amount of purified preen oil.

In another aspect, a food or feed composition comprises 0.01 to 10 wt % of purified preen oil, and a basal food composition. Also included herein is a food or feed additive composition comprising 0.1 to 99 wt % of purified preen oil.

In another aspect, a method of feeding a growing fish comprises feeding the growing fish a fish food composition comprising an effective amount of purified preen oil to improve survival and/or stimulate growth in the growing fish.

In another aspect, a method of reducing a risk of hypoxia in a fish in aquaculture, comprises feeding the fish a fish food composition comprising an effective amount of purified preen oil to reduce the risk of hypoxia in the fish in aquaculture.

In yet another aspect, an aquaculture fish feed composition comprises 0.01 to 10 wt % of purified preen oil, and a basal aquaculture fish feed composition. Also included herein is an aquaculture fish feed additive composition comprising 0.1 to 99 wt % purified preen oil.

In a still further aspect, a method of feeding live prey organisms for use as food in aquaculture comprises feeding the live prey organisms a diet comprising an effective amount of purified preen oil to increase a preen oil lipid content of the live prey organisms.

In a yet further aspect, a pharmaceutical composition comprises 0.1 to 99 wt % of purified preen oil, and a pharmaceutically acceptable excipient.

Figure 1:
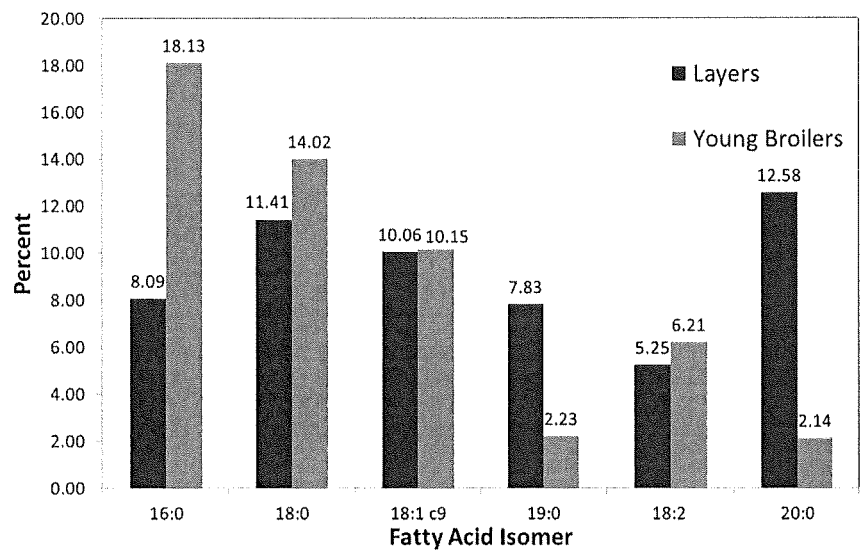
FIG. 1 shows the fatty acid content of preen oil purified from the preen glands of layers and young broilers.

The above-described and other features will be appreciated and understood by those skilled in the art from the following detailed description, drawings, and appended claims.

DETAILED DESCRIPTION

Described herein are methods of orally administering purified preen oil to provide health benefits in humans and animals. The health benefits of orally administered preen oil had not previously been reported. It has been unexpectedly discovered herein that oral administration of purified preen oil has anti-inflammatory and other health benefits in animals. In an aspect, orally administered purified preen oil reduces disease-associated chronic inflammation. In another aspect, orally administered purified preen oil reduces chronic joint inflammation such as that associated with rheumatoid arthritis (RA). In yet another aspect, oral administration of purified preen oil to larval and growing fish, particularly fish growing in aquaculture, results in decreased mortality, improved health, and increased growth.

As used herein, purified preen oil is defined as the lipids isolated from the preen gland of fowl, such as chickens and turkeys. Purified preen oil is substantially free of the non-lipid fraction of preen exudate containing proteins, inorganic salts and cell fragments. Substantially-free means that the preen oil contains less than about 61 wt % of non-lipid components, specifically less than about 50 wt % non-lipid components, and more specifically less than about 20 wt % non-lipid components. While there is some variability in the composition of preen oil depending upon the source and the purification method, in general, preen oil contains 6:0, 7:0, 8:0, 9:0, 10:0, 11:0, 12:0, 13:0, 14:0, 15:0, 16:0, 17:0, 18:0, 18:1 C9, 19:0, 18:2 and 20:0 fatty acids.

In one aspect, a method of treating an individual in need of treatment for chronic inflammation comprises orally administering to the individual a composition comprising a therapeutically effective amount of purified preen oil. As used herein, chronic inflammation is not acute or injury-related and is associated with dysregulation of the pro-inflammatory cytokines IL-1 and IL-6. Inhibition of IL-1 and IL-6 by the administration of preen oil produces broad anti-inflammatory effects. In one aspect, the chronic inflammation is associated with a disease wherein inhibition of the pro-inflammatory cytokines IL-1 and IL-6 reduces disease-associated chronic inflammation. In another aspect, the chronic inflammation is chronic joint inflammation which is generally associated with pain lasting for weeks or even years, or chronic joint inflammation associated with the natural aging process. In a still more specific aspect, the chronic inflammation is associated with a disease associated with chronic joint inflammation such as arthritis.

Individuals within the scope of the present methods include mammals and non-mammals such as fish and birds. Mammals include humans, dogs, equines, and porcines and bovines, for example.

Human diseases wherein inhibition of the pro-inflammatory cytokines IL-1 and IL-6 reduce disease-associated chronic inflammation include autoinflammatory syndromes such as Cryopyrin-associated periodic syndromes (CAPS), familial Mediterranean fever (FMF), Schnitzler's syndrome, adult onset Still's Disease (aoSD), antisynthetase syndrome, relapsing polychondritis, familial cold autoinflammatory syndrome (FACS, FCAS2), Muckle-Wells syndrome (MWS), dermatomyositis (DM), polymyositis (PM), sporadic inclusion body myositis (IBM), necrotizing autoimmune myopathy (NAM), inflammatory bowel disease (IBD), post-infarction inflammation, Tumor Necrosis Factor Receptor Associated Periodic Syndrome (TRAPS), systemic autoinflammatory disease (SAID), NOMID/CINCA, PFAPA (periodic fevers with aphthous stomatitis, pharyngitis, and adenitis) syndrome, recurrent idiopathic pericarditis, Mollaret syndrome, delayed pressure urticaria, pyoderma gangrenosum and acne (PAPA) syndrome, Deficiency of Il-1 Receptor Agonist (Il-1 RA) (DIRA), Majeed Syndrome, CARD14 mediated psoriasis (CAMPS), deficiency of interleukin 36 receptor antagonist (DITRA), Blau's syndrome, Chronic Recurrent Multifocal Osteomyelitis (CRMO), Synovitis, Acne, Pustulosis, Hyperostosis and Osteitis (SAPHO) Syndrome, HLA-B27 spondyloarthropathy, Sweet syndrome, generalized pustular psoriasis, Hallopeau acrodermatitis, Nakajo-Nishimura syndrome, Joint contractures, muscle atrophy, microcytic anemia and panniculitis-induced lipodystrophy (JMP) syndrome, Chronic atypical neutrophilic dermatosis with lipodystrophy and elevated temperature (CANDLE) syndrome, early-onset inflammatory bowel disease, neutrophilic panniculutis, Erythema nodosumand panniculitis, Crohn's disease. Microphage activation syndromes (MAS), familial hematophagocytic lymphohistiocytosis, and Castleman's disease.

Chronic joint inflammation in humans is associated with rheumatoid arthritis (RA), systemic lupus erythematosus, reactive arthritis, lupus arthritis, arthritis associated with Sjogrens syndrome, systemic onset juvenile idiopathic arthritis (SOJIA), gout, pseudogout, osteoarthritis, psoriatic arthritis, peripheral joint inflammation associated with inflammatory bowel disease, Ankylosing spondylitis, reactive arthritis, age-related joint degeneration, or chronic Lyme disease, for example. In one aspect, the individual is a human individual.

Orally administered therapeutically effective amounts of purified preen oil for the treatment of chronic inflammation in humans are 0.001 to 100 g per day, specifically 0.025 to 25 g per day. In one aspect, preen oil is orally administered to a human in an amount of greater than or equal to 25 mg per day. Since preen oil is safe for consumption, there should be no toxicity associated with the higher ranges. Higher ranges are preferred for more rapid incorporation in tissues and low ranges for long-term use.

In another aspect, the individual is a companion animal such as a dog, or a livestock animal such as cattle. Dogs, equines, porcines and cattle suffer from diseases associated with chronic inflammation such as osteoarthritis, chondrodystropy, arthritis, osteochondrosis, spondylosis, intervertebral disk disease, diskopondylitis, degenerative arthropathy, hip dysplasia and chronic laminitis. Dogs are known to suffer from chronic joint inflammation due to arthritis and pigs, horses, and cattle suffer from chronic joint inflammation due to lameness. Orally administered therapeutically effective amounts of purified preen oil for the treatment of chronic inflammation in dogs and cattle are 0.0001 to 450 g per day, specifically 0.001 to 145 g per day. These ranges are based on metabolic scaling where the low end would be the minimal levels for a 1 Kg dog and the high range for a 750 Kg cattle. In a specific aspect the purified preen oil is orally administered in an amount of greater than or equal to 1 mg per day.

Exemplary compositions for the oral administration of purified preen oil include pharmaceutical compositions as well as food compositions such as nutraceutical food compositions, described in more detail below.

Low-grade chronic inflammation underpins many diseases affecting human health such as RA and remains largely undiagnosed and undertreated worldwide. Without being held to theory, it is believed that fatty acids such as those found in purified preen oil will accumulate in body cells and tissues after oral consumption, thus purified preen oil is predicted to be an effective oral treatment for reducing damaging effects of chronic inflammation, including chronic joint inflammation, such as joint destruction in RA.

Specifically, the anti-inflammatory effects of dietary purified preen oil were studied in a model of chronic inflammation associated with dysregulation of the pro-inflammatory cytokines IL-1 and IL-6. Chronically inflamed arthritic mice over a 9 week period using the collagen-induced arthritis model were used. As shown in the examples, the results from this pre-clinical animal study demonstrate the efficacy of purified preen oil as an oral anti-inflammatory agent. Similar results are expected for the treatment of all types of chronic inflammation and diseases associated with chronic inflammation and more specifically chronic joint inflammation such as arthritis.

Further included herein are feed/food compositions and feed/food additives comprising purified preen oil. As used herein, the term "food composition" and "food additive" refer to compositions for ingestion by a human while "feed composition" and "feed additive" refer to compositions for ingestion by an animal.

In an aspect, a food or feed composition comprises 0.001 to 50 wt % specifically, 0.01 wt % to 10 wt %, and more specifically 0.1 wt % to 5 wt % of purified preen oil, wherein the food composition comprises a basal food composition and is suitable for ingestion by a human, and the feed composition comprises a basal feed composition and is suitable for ingestion by an animal. In one aspect, a basal food or feed composition is a nutritionally complete food or feed composition.

As used herein, the terms "food" and "feed" broadly refer to a material, liquid or solid, that is used for nourishing a human or animal. Feed compositions, for example are used for sustaining normal or accelerated growth of an animal including newborns or young and developing animals. The terms include a compound, preparation, mixture, or composition suitable for oral intake by a human or animal. Feeds are suitable for herbivorous mammals such as cattle, horses, sheep and goats; for fish and poultry; or for companion animals, for example. A food/feed composition comprises a basal food/feed composition and one or more food/feed additives. The term "basal food/feed composition" refers to a food/feed composition combinable with purified preen oil described herein. The term "feed/food additive" as used herein refers to components included in small quantities for the purpose of fortifying basic feed/food with nutrients, stimulants, medicine, or to promote feed intake or alter metabolism. As a general rule, feed/food additive are added to a basal feed/food composition in an amount of 0.01 to 10 wt % based on the weight of the basal feed/food composition. Feed/food additives include pre-mixes of biological compositions, or in the present disclosure, compositions containing purified preen oil and optionally at least one additional edible component.

Basal feed compositions may include components such as a protein source, a grain, flavor compositions, vitamins, minerals, preservatives, and combinations thereof. Basal feed compositions can be suitable for ingestion by a target animal.

An animal feed may further include optional ingredients including vitamins, minerals, antibiotics, lipids, carbohydrates, proteins, antioxidants, and amino acids.

Exemplary vitamins include Vitamin A, Vitamin B, Vitamin D, Vitamin E, and Vitamin K. Exemplary minerals include calcium, phosphorus, sodium, potassium, magnesium, chlorine, cobalt, iodine, iron, manganese, copper, molybdenum, zinc and selenium. Common mineral supplements used in poultry feed, for example, include limestone, bone meal, oyster shell, sodium chloride, dicalcium phosphate, manganese sulphate, potassium iodide, and superphosphate.

In some embodiments, one or more antibiotics may be included in the animal feed along with the feed additive. Exemplary antibiotics include penicillin, streptomycin, tetracyclines, zinc bacitracin and aureomycin.

Exemplary lipids include oil seeds, oils and lipids derived from plants or animals. Sources of oilseeds, oils and lipids include corn, soybean, cotton, lupin, peanut, sunflower, canola, sesame seed oil, olive oil, copra and coconut oil, palm kernels and palm oil, casein, butterfat, lard, fish oils, linseed and oil, tuna oil, tallow and yellow grease, and mixtures thereof.

Exemplary carbohydrates include starch, cellulose, pentosans, other complex carbohydrates, corn, milo, barley, rye, oats, wheat, wheat middlings, and various grain-by-products.

Exemplary sources of protein include protein obtained from meat meal or fish meal, liquid or powdered egg, fish solubles, whey, milk protein, rice, milo, millet, corn, oats, barley, wheat, rye, wheat bran and/or middlings, soybeans, sesame seeds, peas and beans, sunflower seeds, wheat germ, alfalfa seed, flaxseed, yeast, earthworms, and fish.

Exemplary amino acids include arginine, histidine, isoleucine, leucine, lysine, methionine, phenylalanine, threonine, tryptophan, valine, tyrosine ethyl HCl, alanine, aspartic acid, sodium glutamate, glycine, proline, serine, cystein ethyl HCl, and analogs, and salts thereof.

Exemplary antioxidants include beta-carotene, Vitamin E, Vitamin C, and tocopherol, or synthetic antioxidants.

In another aspect, included herein is a food composition suitable for administration to humans containing a basal food composition and purified preen oil. As used herein, the term "food" or "food product" refers to a food suitable for consumption by humans. The "food product" may be a prepared and packaged food (e.g., milk, yogurt, or cheese). Food products include prepared food products. "Prepared food product" means a pre-packaged food approved for human consumption.

An exemplary food product is a dietary supplement such as a powder, liquid concentrate, bar or shake. Powders and concentrates can be added to a liquid such as water or milk for consumption. In addition to purified preen oil, the dietary supplement can comprise additional components such as vitamins, minerals, amino acids and protein sources.

In another aspect, a functional food or feed additive composition comprises 0.001 to 99 wt %, specifically, 0.01 wt % to 95 wt % of purified preen oil, wherein the functional food additive composition comprises a basal functional food additive composition and is suitable for ingestion by a human, and the functional feed additive composition comprises a basal functional feed additive composition and is suitable for ingestion by an animal. A 100% purified preen oil food or feed additive composition could, for example, be in the form of a capsule. As used herein, a functional food/feed additive is a functional edible substance that is not consumed as a food itself, but that is added to food to provide or maintain nutritive value. Essentially, a functional food/feed additive is a dietary supplement that is added directly to a food or feed composition to improve the properties of the food or feed composition or the health of the animal. Basal functional food/feed additives include, vitamins, minerals enzymes, essential oils, acidifiers prebiotics, probiotics, botanical products yeast and yeast fractions, as well as carriers.

In another aspect, included herein are pharmaceutical compositions comprising preen oil. For example, a pharmaceutical composition comprises 0.001 to 99 wt %, specifically 0.1 wt % to 99 wt % of purified preen oil, and a pharmaceutically acceptable excipient.

Tablets and capsules for oral administration may be in unit dose form, and may contain conventional excipients such as binding agents, for example syrup acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice.

Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavoring or coloring agents.

In another aspect, a method of feeding a growing fish comprises, feeding the growing fish a fish food composition comprising an effective amount of purified preen oil to improve survival and/or stimulate growth in the growing fish. As used herein, the term fish includes finfish and shellfish such as shrimp. The term growing fish means fish that are increasing in length and weight in time. Exemplary growing fish are larval and juvenile fish. New methods to improve fish growth and survival are needed, and in particular additives for fish feed that can improve survival and/or growth and that are stable to the fish feed production process. Growth can be measured as the length of the fish, such as the average length of fish in a population.

In a specific aspect, the fish is in aquaculture. As used herein, aquaculture means the active cultivation of aquatic organisms under controlled conditions. Aquaculture systems use water as the medium for cultivation. An aquaculture system must provide clean and oxygenated water to support the cultivated organisms as well as a means to remove deoxygenated water and wastes. As used herein, aquaculture includes both marine and freshwater aquaculture. Typical aquaculture systems include holding tanks and means for filtering, dissolved gas control, and temperature control. Aquaculture typically requires a prepared aquaculture feed composition to meet dietary requirements of the cultured animals.

Basal aquaculture fish feed compositions, for example, contain a protein source such as fish meal. Due to problems securing fish to produce fish meal and the depletion of fish stock for feeding fish, attempts have been made to supplement fish foods with other proteins. Soy protein is commonly used as a protein source in basal fish feeds, however soy protein induces gut inflammation and increases proinflammatory cytokines. These cytokines are linked to decreased food intake and growth. Researchers have been trying to find ways to counteract the proinflammatory effects of certain alternative fish foods. An advantage of the use of purified preen oil in fish food compositions for aquaculture is that it reduces proinflammatory processes known to reduce growth and can reduce the negative effects of commonly available protein sources such as soy protein High valued fish for aquaculture applications (carp, tilapia, hybrid striped bass, salmon, trout, catfish, yellow perch, walleye; marine species such as cod, cobia, sea bass, tuna, and sole; and shellfish such as shrimp, scallops and oysters for example) may have poor larval growth and high rates of mortality, which is delaying the expansion of the aquaculture industry. In particular, there can be high mortality rates of up to 95% at the larval stage. Inflammation of the gastrointestinal tract has been shown to slow growth in fish species. New methods to improve fish growth are needed. Purified preen oil can be added to a fish feed or a fish feed pre- or post-pellet formation and can either be added on the diet or as a replacement for some of the lipid in the fish food.

In experiments described herein, larval and fish food pellets served as a control or were coated with 2% preen oil. The fish were fed the two diets in 4 tanks each and growth was measured by length increases. The experiment lasted 30 days. Larval fish fed the preen oil had a 27% increase in growth (P=0.02). In addition, preen oil improve survival in fish exposed to hypoxic conditions, demonstrating that preen oil reduces the susceptibility of the fish to stress and increases their chances of survival in culture.

In another aspect, a diet containing purified preen oil was found to reduce hypoxia in fish in aquaculture that were subjected to hypoxic conditions. A method of reducing the risk of hypoxia in a fish in aquaculture comprises feeding the fish a fish food composition comprising an effective amount of purified preen oil to reduce the risk of hypoxia in the fish in aquaculture. In one aspect, the fish have been exposed to hypoxic conditions or are at risk of being exposed to hypoxic conditions. Hypoxia is a known problem in aquaculture, particularly pond aquaculture, where fish are often raised at high densities. During the day when the algae in the ponds are photosynthesizing, there is typically enough oxygen in the ponds. At night, however, the algae start to respire and oxygen levels can drop dramatically. Some or all fish often die overnight due to hypoxia, which is why many commercial aquaculture facilities rely on aerators to oxygenate the ponds overnight. The ability of preen oil to protect fish from hypoxia in aquaculture is a significant discovery.

In one aspect, the fish food composition comprises 0.01 wt % to 10 wt %, specifically, 0.1 wt % to 2 wt % of purified preen oil on a w/w basis and a basal fish feed composition. In a more specific aspect, included herein is an aquaculture fish feed composition containing purified preen oil and a basal aquaculture fish feed composition. The aquaculture fish feed composition comprises 0.01 wt % to 10 wt %, specifically, 0.1 wt % to 2 wt % of purified preen oil. Typical components in a basal fish feed or aquaculture fish feed composition include proteins and carbohydrates, based on fish meal, soybean meal or vegetable/corn meal, and may be supplemented with essential amino acids, proteins, peptides, vitamins, minerals, carbohydrates, fats, oils, and combinations thereof. Vitamins include A, E, K, $D_3$, $B_1$, $B_3$, $B_6$, $B_{12}$, C, biotin, folic acid, panthothenic acid, nicotinic acid, choline chloride, inositiol, and para-amino-benzoic acid. Minerals include salts of calcium, cobalt, copper, iron, magnesium, manganese, phosphorus, potassium, selenium and zinc. Other components may include, but are not limited to, antioxidants, beta-glucans, bile salt, cholesterol, enzymes, monosodium glutamate, and the like. Basal aquaculture fish feed compositions are prepared products generally in the form of flakes, pellets or tablets that form a nutritionally complete diet for the aquacultured species. The purified preen oil can be added during production of the aquaculture fish feed composition so that it is substantially homogeneously distributed throughout the aquaculture fish feed composition, or the purified preen oil can be added to a pre-prepared basal aquaculture fish feed composition for example by top dressing.

In other aspect, soy is used as a protein source in a basal fish feed composition. Soybeans in the form soy flours, soy flakes, and soy meal generally have off-flavors that are unpalatable to aquacultured fish due to their relatively higher antigenicity. Fish feed compositions containing purified preen oil may allow for the use of higher amounts of soy protein in fish food compositions.

The importance of providing a sufficient amount of lipids for successful production of marine fish larvae is known in the art. The two main live feeds used for marine fish larval production, rotifers and Anemia (brine shrimp nauplii), naturally lack certain long chain polyunsaturated fatty acids and highly unsaturated fatty acids must be supplemented to ensure successful survival, growth and metamorphosis of the larvae. A major source of long chain polyunsaturated fatty acids for live feed supplementation is fish oils. Saturated and monounsaturated fatty acids have also been identified as major energy yielding nutrients in fish. U.S. Pat. No. 7,063,855 describes feeding lipids to aquacultural prey organisms to improve the highly-unsaturated fatty acid content of the live food.

Also included herein are aquaculture fish feed additive composition comprising purified preen oil, such as 0.1 to 99 wt % purified preen oil. The aquaculture fish feed additives optionally include an edible component in addition to the purified preen oil.

As an alternative to feeding fish a feed containing purified preen oil, fish can be fed live prey organisms that have been fed a diet containing purified preen oil. In one aspect, a method of feeding live prey organisms for use as food in aquaculture comprises feeding the live prey organisms a diet comprising an effective amount of purified preen oil to increase a preen oil lipid content of the live prey organisms. In an aspect, the diet for the live prey organisms comprises 0.1 wt % to 50 wt %, specifically 1 wt % to 10 wt % of purified preen oil based on the total weight of the diet. In another aspect, the preen oil fatty acid content of the live prey organisms that have been fed purified preen oil is 0.01 to 10% of total fatty acids of the prey.

In another aspect, a method of feeding a growing fish such as a larval or juvenile fish, comprises feeding the growing fish live prey organisms that have been fed a diet comprising an effective amount of purified preen oil to increase a preen oil lipid content of the live prey organisms. In one aspect, the growing fish are in aquaculture. Amounts of purified preen oil in the diet of the live prey organisms include 0.1 wt to 50 wt %, specifically 1 wt % to 10 wt %, purified preen oil based on the total weight of the diet. Live prey organisms include Anemia, rotifers and zooplankton. The diet of live prey organisms can contain similar components to the basal fish feed compositions described herein.

The invention is further illustrated by the following non-limiting examples.

EXAMPLES

Example 1: Purification of Preen Oil from Preen Glands

Preen glands were removed from tails of laying hens and broilers using mechanical means, cut open, and gland contents were removed. The preen lipids were extracted from the gland contents by heating to an internal temperature of 80° C. and centrifugation at 3,000×g for 40 minutes, and the fractions were analyzed using thin layer chromatography and gas chromatography (GC) for fatty acid composition. The amount of preen oil isolated from laying hens varied from 0.09-0.79 g of oil per preen gland. The amount of preen oil isolated from broilers varied from 0.05-0.21 g of oil per preen gland. The fatty acid content of purified preen oil is provided in FIG. 1.

Preen oil was also isolated from turkey preen glands and the amount of preen oil is given in table 1.

TABLE 1

Preen oil isolated from turkey preen glands

| Type of Sample | Number of Samples Collected | Mean Weight of Total Oil Material Per Gland |
|---|---|---|
| Young Turkey raised at UW Madison | 13 | 0.13 |
| Turkey Toms | 10 | 0.73 |

Example 2: Anti-Inflammatory Activity of Purified Preen Oil in Collagen Induced Arthritis Mouse Model Methods:

Collagen-induced arthritis model. Four-week-old male DBA/1 mice (n=72) were purchased (Harlan, Indianapolis, Ind.) and housed in shoebox units (3 mice per box) with a 12:12 hour light-dark cycle. Mice were fed a standard rodent diet (8604, Harlan, 24.5% protein, 4.4% fat, 46.6% nitrogen-free extract) during a 7 day environmental acclimation period. After the acclimation period, mice were switched to a 97% complete, casein-based, semi-purified diet (based on the AIN-76A diet; TD140724) supplemented with 3% corn oil (CO) as the principle dietary fat (100% nutritionally replete after 3% CO addition). CO has been used as a reference dietary lipid source in multiple collagen-induced arthritis studies. In some studies, canola oil (CA) was used in place of corn oil.

After 3 weeks of maintenance on the CO diet, mice were immunized as previously described to induce arthritis. Briefly, 8 week old mice were randomized into two groups for immunization against chick type II collagen (tIIc, Chondrex, Redmond, Wash., n=45), or 0.05M acetic acid (sham non-arthritic, n=27) emulsified with complete Freund's adjuvant (4 mg/ml *M tuberculosis* H37RA). After a booster injection 3 weeks later, mice were monitored daily for clinical signs of arthritis (see clinical arthritic score). In order to prevent excessive handling, arthritic mice were assessed for severity three times per week after diagnosis.

When the first mouse in a cage developed positive clinical signs of arthritis (designated day 0), it was randomly assigned to one of the following dietary treatments: (1) 3% CO diet, (2) 3% CA diet, or (3) 3% preen oil diet. Because the onset of arthritis occurs unpredictably, dietary treatments were initiated post-onset only. Specifically, the first arthritic mouse in a box was randomly reassigned to a dietary treatment in a new cage. The remaining mice in the original cage were relocated to the new cage only after development of arthritis. Arthritic and sham-immunized mice (maintained on the CO diet) remained on dietary treatments for 63 days. Throughout the dietary treatment period, clinical arthritic score (described below) was monitored three times per week, per mouse. Additionally, paw thickness measurements (described below) were recorded once per week upon and post-development of arthritis.

Clinical Arthritic Score.

Mice were examined three times per week by a trained observer blinded to treatment as detailed previously. Individual paws were assigned a score based on the following criteria: 0=normal: no inflammation; 1=mild: definite redness and swelling of the ankle or wrist or apparent redness and swelling limited to individual digits, regardless of the number of affected digits; 2=moderate: redness and swelling of ankle and wrist; 3=severe redness and swelling of the entire paw including digits; 4=maximally inflamed limb involving multiple joints. The sum of all four paws was calculated, averaged between the two observers, and reported as the "clinical arthritic score".

Paw Thickness Measurements.

Immediately upon onset of arthritis and weekly thereafter, individual paw thickness was recorded using a pressure sensitive caliper (SPI, Garden Grove, Calif.) as an adjunct to clinical arthritic score.

Paw Tissue Preparation.

On day 63 immediately after mice were euthanized by exsanguination, front and hind paws were harvested, snap frozen in liquid nitrogen, and separately weighed then crushed under liquid nitrogen. Total protein was extracted by tissue homogenization using T-PER® tissue protein extraction reagent with Halt™ protease inhibitor cocktail (Thermo, Rockford, Ill.) including the following proteases: AEBSF (1 mM), Aprotinin (800 nM), Bestatin (50 uM), E64 (15 uM), Leupeptin (20 uM), Pepstatin A (10 uM), and EDTA (5 mM) at 10:1 v/w buffer to paw tissue. Samples were incubated on ice for 1 hour and centrifuged at 3,000 RPM for 10 minutes at 4° C. Supernatant was collected and centrifuged at 16,000×g at 4° C. for 45 minutes. Avoiding the top lipid layer, supernatant was collected and stored at −80° C. Total protein content was determined using a BCA protein assay (Thermo, Rockford, Ill.) prior to cytokine quantitation. Samples were diluted to a final protein concentration less than 1 mg/ml.

Cytokine analysis. Paw tissue concentrations of interleukin (IL)-1β, IL-6, IL-10 and tumor necrosis factor (TNF)-α were measured using the mouse Bio-Plex Pro™ cytokine assay system according to the manufacturer's specifications (Bio-Rad Laboratories, Hercules, Calif.). Fluorescence was measured using the Luminex 100™ system (Bio-Rad Laboratories) and results were analyzed using Bio-Plex Manager™ software (Bio-Rad Laboratories). Cytokine concentrations for each tissue were normalized to the respective total protein content for that sample and reported as ng/g of tissue protein.

Fatty Acid Determination.

Total lipids from both dietary fat sources and paws were extracted using chloroform/methanol (2:1 v/v) according to methods known in the art, with the exception that paws were crushed and cut into approximately 3 mm×3 mm pieces prior to homogenization. Fatty acid methyl esters were prepared by acid-catalyzed methylation. Relative percentages of fatty acid methyl esters were determined using an Agilent 6890N GC (Agilent Technologies, Santa Clara, Calif.) equipped with a Restek Rt®-2560 100m biscyanopropyl polysiloxane column (Restek, Bellefonte, Pa.).

Figure 2:
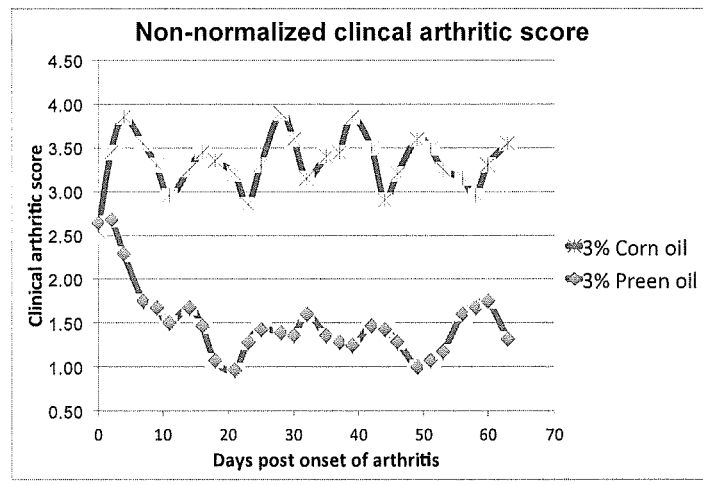
FIG. 2 shows the clinical arthritic score over a 63-day period for mice supplemented with 3% preen oil compared to 3% corn oil.
Figure 3:
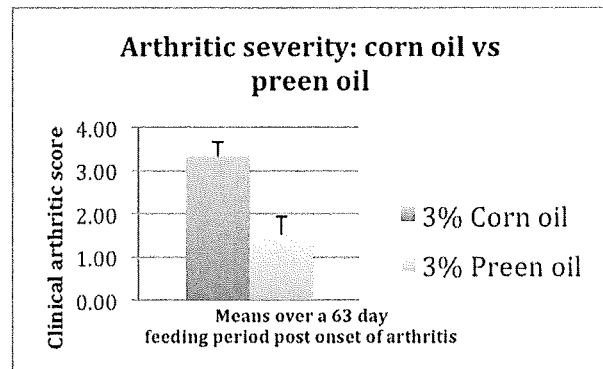
FIG. 3 shows the reduction in arthritic severity over a 63-day period for mice supplemented with 3% preen oil compared to 3% corn oil.

Results:

As shown in FIG. 2, dietary preen oil supplemented at 3% (w/w) reduced the clinical arthritic score in the collagen induced murine model of rheumatoid arthritis. DBA/1 mice were fed diets containing 6% total fat supplemented with either 3% corn oil or 3% preen oil for 63 days post-onset of arthritis. A blinded observer scored severity of arthritis three times per week. Each point represents group means at each day; 3% preen oil (n=7), 3% corn oil (n=5). FIG. 3 shows the average reduction in arthritic severity over a 63-day period post onset of disease. Dietary preen oil fed at 3% w/w reduced arthritic severity 55% compared to a 3% corn oil supplemented diet. Values are means±standard deviation.

Figure 4:
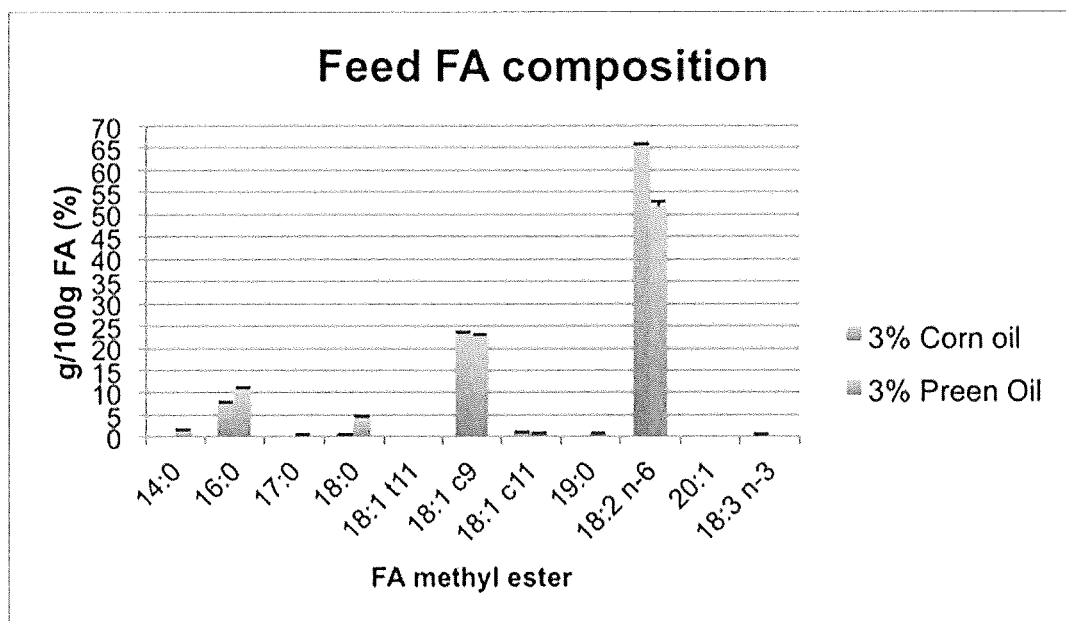
FIG. 4 shows the feed fatty acid composition for a 3% corn oil and a 3% preen oil mouse diet.

FIG. 4 shows a comparison of 3% preen oil and corn oil diet fatty acid compositions. Diets contained 6% total fat with corn oil making up the basal fat. Means are grams of fatty acid per 100 g total fat±SEM. Not pictured: 3% preen oil diet contains a total of 8% of saturated fatty acids 5:0-12:0. Table 2 shows the hind paw fatty acid composition of sham mice fed 3% preen oil or 3% corn oil over a 63 day period. Table 2 shows that after oral administration of preen oil FAs not present in corn oil, such as 12:0, 17:0, 17:1, and 19:0, are increased in the paws of mice suggesting that orally administered preen oil accumulates at the site of inflammation.

TABLE 2

Hind paw fatty acid composition of sham mice fed 3% preen oil or 3% corn oil over a 63 day period.

| Fatty acid | 3% Corn Oil g/100 g FA | 3% Preen Oil g/100 g FA | Pooled SEM |
|---|---|---|---|
| 12:0 | ND | 0.04 | 0.01 |
| 14:0 | 0.73 | 1.50 | 0.04 |
| 14:1 | 0.10 | 0.22 | 0.01 |
| 15:0 | 0.01 | 0.07 | 0.01 |
| 16:0 | 8.92 | 11.71 | 0.47 |
| 16:1 | 13.92 | 18.30 | 0.72 |
| 17:0 | ND | 0.09 | 0.01 |
| 17:1 | ND | 0.27 | 0.01 |
| 18:0 | 0.58 | 0.76 | 0.04 |
| 18:1 c9 | 40.83 | 39.40 | 0.38 |
| 18:1 c11 | 3.04 | 3.43 | 0.08 |
| 18:2 n-6 | 29.64 | 21.37 | 0.47 |
| 18:2 c9t11-CLA | 0.06 | ND | 0.01 |
| 18:3n-3 | 0.19 | 0.18 | 0.02 |
| 19:0 | ND | 0.05 | 0.01 |
| 20:0 | 0.10 | 0.12 | 0.01 |
| 20:1n-9 | 0.37 | 0.39 | 0.01 |
| 20:2n-6 | 0.04 | 0.05 | 0.01 |
| 20:4n-6 | 0.28 | 0.33 | 0.01 |
| 22:6n-3 | 0.07 | 0.07 | 0.01 |
| Unknown | 1.42 | 1.70 | 0.22 |
| Total Identified | 98.58 | 98.30 | 0.03 |

Values are means (n = 3/group).
ND, non detectable

Figure 5:
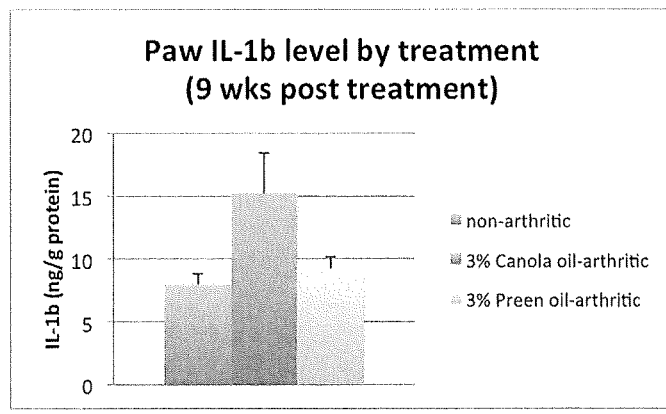
FIG. 5 shows mouse paw IL-1β in non-arthritic mice, arthritic mice supplemented with 3% canola oil, and arthritic mice supplemented with 3% preen oil.
Figure 6:
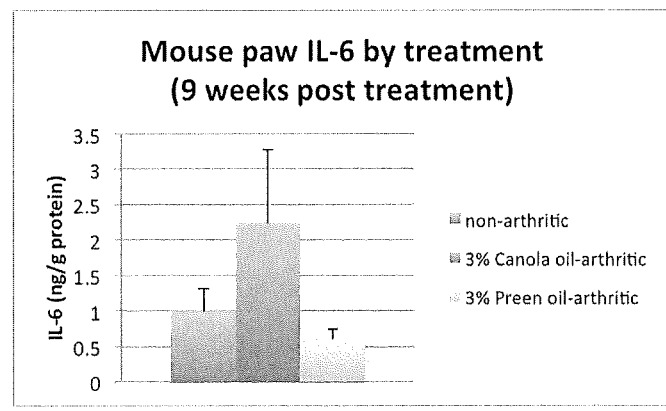
FIG. 6 shows mouse paw IL-6 in non-arthritic mice, arthritic mice supplemented with 3% canola oil, and arthritic mice supplemented with 3% preen oil.

After 9 weeks of arthritis monitoring, paws were examined for proinflammatory cytokine levels. FIG. 5 shows that 3% preen oil reduced IL-1β to much lower levels than canola oil, and close to the levels seen in non-arthritic mice. FIG. 6 shows that 3% preen oil reduced IL-6 to much lower levels than canola oil, and lower than the levels seen in non-arthritic mice. These data are consistent with reduced arthritis in mice fed preen oil in that paw proinflammatory cytokines were reduced to sham levels in these mice.

Figure 7:
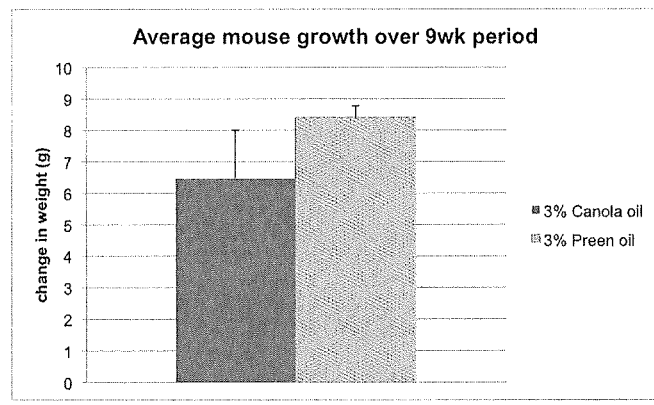
FIG. 7 shows the average mouse weight gain over a 63-day period in 8 week old, weight matched mice fed either 3% canola oil diet or 3% preen oil diet and weighed weekly.

Example 5: Effects of Preen Oil on Mouse Growth 8 week old, weight-matched mice were fed either a 3% CA diet or a 3% preen oil diet and weighed weekly over a 63-day period. As shown in FIG. 7, mice fed 3% preen oil had a 30% increase in weight gain vs mice fed 3% CA, suggesting that dietary preen oil increases growth rate or weight gain. Upon further examination several weeks later, increased growth rate did not result in an increased fat mass compared to mice fed 3% CA diet. This observation suggests preen oil may increase growth rate without increased fat deposition in adipose or an associated lipodystrophy.

Example 4: Effects of Preen Oil on the Growth and Survival of Larval Fathead Minnows Fed Exclusively on Formulated Diet Methods:

Experimental System.

Eight 7-L glass aquariums (tank water volume was 6 L) with flow-through water (carbon-filtered City of Madison, Wis. water). The temperature was 25±0.5° C. The flow rate into each tank was 250 ml/min (2.5 tank turnovers per hour). Each tank had an air stone.

Fish.

Fifty newly hatched fathead minnows were added to each tank on day 0. The fish were obtained from the colony maintained at the UW-Madison Aquaculture Research Laboratory.

Feed.

Larval fathead minnows are typically fed live *Artemia*, but for this experiment the fish were only fed dry, formulated diet (Skretting, Gemma Micro 150) to ensure that all fish fed on the treated diet.

Experimental Design.

A randomized block design was used for the experiment. There were two blocks (upper or lower shelf), and two treatment groups: (1) control and (2) fed with diet top-coated with 2% preen oil. There were four tanks per treatment group and treatments were randomized within block. The fish in each tank were fed twice daily (morning and afternoon) an excess of feed. Tanks were cleaned approximately weekly or as needed.

Data Collection.

The lengths of the fish were measured on day 0, 1 and 2 months using digital photos taken of each tank and a digital ruler (Pixelstick).

Figure 8:
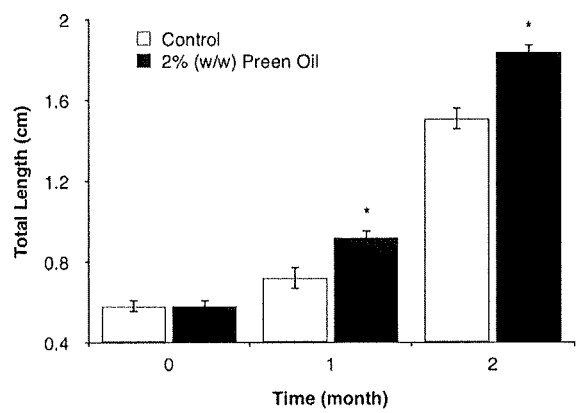
FIG. 8 shows the effects of 2% dietary preen oil on the growth of larval fathead minnows.
Figure 9:
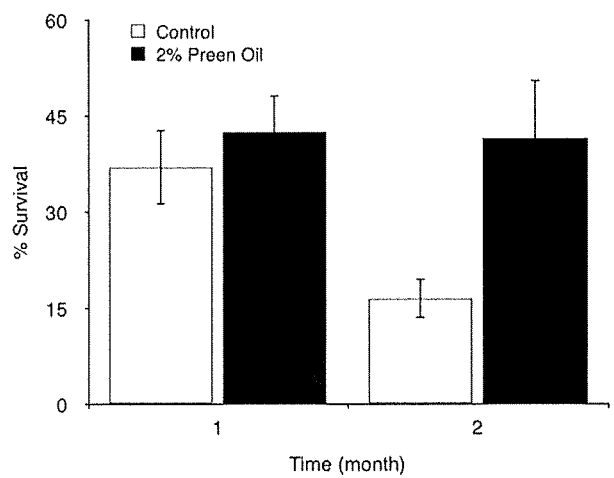
FIG. 9 shows the effects of 2% dietary preen oil on the survival of larval fathead minnows.

Results:

At month one, the larval fish fed the control and 2% preen oil diets were 0.72±0.6 and 0.92±0.04 cm in length, respectively (FIG. 8). This difference was significant at P=0.03 (paired, two-tailed t-test). At month two, the larval fish fed the control and 2% preen oil diets were 1.51±0.02 and 1.84±0.02 cm in length, respectively. This difference was significant at P=0.05 (paired, two-tailed t-test). Larval survival at the end of the experiment in the control and 2% preen oil groups were 16.5±3.1% and 41.5±9.1%, respectively (FIG. 9). Thus, the diet including preen oil increased larval fish growth measured as total length and also significantly improved survival after one and two months.

Example 5: Effects of Preen Oil on the Survival of Hypoxic Juvenile Walleye

Methods:

Experimental System.

Fifteen 7-L glass aquariums (tank water volume was 6 L) with flow-through water (carbon-filtered City of Madison, Wis. water). The temperature was 25±0.5° C. The flow rate into each tank was 250 ml/min (2.5 tank turnovers per hour).

Experimental Design.

A randomized design was used. There were three treatment groups: (1) control, (2) tallow oil iso-caloric control, and (3) 2% preen oil. There were five tanks per treatment group, each stock with five juvenile walleye (approximately 2.3 g each at the start of experiment). The fish in each tank were fed twice daily (morning and afternoon) at a rate of approximately 5% of their body weight daily. The fish were fed (Skretting, Gemma Diet, 1 mm).

Results

Figure 10:
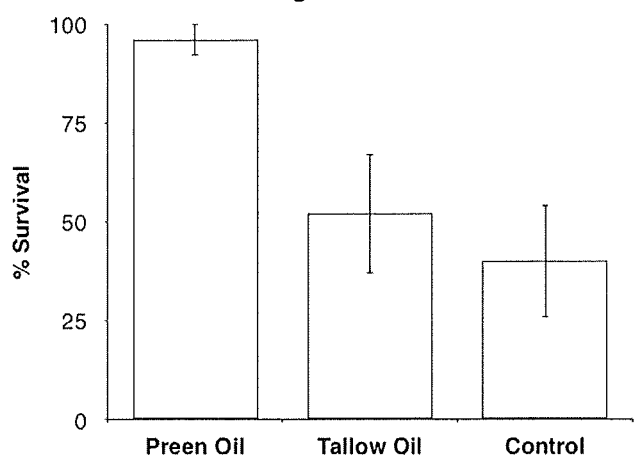
FIG. 10 shows the survival rates of juvenile walleyes subjected to acute hypoxia.

Fifteen days after the start of the experiment, the water to the fish tanks was turned off to prevent a change in water temperature during repairs to the lab's hot water system. The air to the tanks, however, was also mistakenly turned off and the environmental conditions in the tanks rapidly became hypoxic. By the time this was discovered, many fish had died or were severely stressed. The percent survival by treatment group was as follows: Control (40%), Iso-caloric tallow oil control (52%), preen oil (96%) (FIG. 10). The differences were highly significant (P<0.02 between preen oil and control and preen oil and iso-caloric control). The average fish weight of the fish on day 15 was 3.6+0.1 g. There was no significant treatment effect on growth at this time.

The use of the terms "a" and "an" and "the" and similar referents (especially in the context of the following claims) are to be construed to cover both the singular and the plural, unless otherwise indicated herein or clearly contradicted by context. The terms first, second etc. as used herein are not meant to denote any particular ordering, but simply for convenience to denote a plurality of, for example, layers. The terms "comprising", "having", "including", and "containing" are to be construed as open-ended terms (i.e., meaning "including, but not limited to") unless otherwise noted. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Any combination of the above-described elements in all possible variations thereof is encompassed by the invention unless otherwise indicated herein or otherwise clearly contradicted by context.

The invention claimed is:

1. A method of feeding a growing fish, comprising feeding the growing fish a fish food composition comprising an effective amount of purified preen oil to improve survival and/or stimulate growth in the growing fish,
wherein the purified preen oil comprises 16:0, 18:0, 18:1 c9, 19:0, 18:2 and 20:0 fatty acids.

2. The method of claim 1, wherein the food composition comprises 0.01 to 10 wt % purified preen oil on a w/w basis.

3. The method of claim 1, wherein the fish is in aquaculture.

4. The method of claim 1, wherein the fish is a finfish or a shellfish.

5. The method of claim 4, wherein the fish is carp, tilapia, hybrid striped bass, salmon, trout, catfish, yellow perch, walleye, cod, cobia, sea bass, tuna, sole, shrimp, scallops or oysters.

6. The method of claim 1, wherein growth in the growing fish is the average length of a population of growing fish.

7. The method of claim 6, wherein the growing fish is a larval or juvenile fish.

8. The method of claim 7, wherein the food composition comprises 0.01 to 10 wt % purified preen oil on a w/w basis.

9. The method of claim 7, wherein the fish is in aquaculture.

10. The method of claim 7, wherein the fish is a finfish or a shellfish.

11. The method of claim 10, wherein the fish is carp, tilapia, hybrid striped bass, salmon, trout, catfish, yellow perch, walleye, cod, cobia, sea bass, tuna, sole, shrimp, scallops or oysters.

12. The method of claim 7, wherein growth in the growing fish is the average length of a population of growing fish.

13. A method of reducing a risk of hypoxia in a fish in aquaculture, comprising
feeding the fish a fish food composition comprising an effective amount of purified preen oil to reduce the risk of hypoxia in the fish in aquaculture,
wherein the purified preen oil comprises 16:0, 18:0, 18:1 c9, 19:0, 18:2 and 20:0 fatty acids.

14. The method of claim 13, wherein the food composition comprises 0.01 to 10 wt % purified preen oil on a w/w basis.

15. The method of claim 13, wherein the fish is a finfish or a shellfish.

16. The method of claim 15, wherein the fish is carp, tilapia, hybrid striped bass, salmon, trout, catfish, yellow perch, walleye, cod, cobia, sea bass, tuna, sole, shrimp, scallops or oysters.

17. The method of claim 13, wherein the fish is a larval or juvenile fish.

18. A method of feeding live prey organisms for use as food in aquaculture, comprising feeding the live prey organisms a diet comprising an effective amount of purified preen oil to increase a preen oil lipid content of the live prey organisms, wherein the purified preen oil comprises 16:0, 18:0, 18:1 c9, 19:0, 18:2 and 20:0 fatty acids.

19. The method of claim 18, wherein the diet comprises 0.1 wt % to 50 wt % of purified preen oil based on the total weight of the diet.

20. A method of feeding a growing fish, comprising
feeding the growing fish live prey organisms that have been fed a diet comprising an effective amount of purified preen oil to increase a preen oil lipid content of the live prey organisms.

21. The method of claim 20, wherein the growing fish are larval or juvenile fish.

22. The method of claim 20, wherein the diet of the prey organism comprises 0.1 wt % to 50 wt % of purified preen oil based on the total weight of the diet.

23. The method of claim 22, wherein the growing fish are in aquaculture.

24. The method of claim 22, wherein the live prey organisms are *Artemia*, rotifers or zooplankton.

\* \* \* \* \*